(12) United States Patent
Copeland et al.

(10) Patent No.: US 7,969,715 B2
(45) Date of Patent: Jun. 28, 2011

(54) POWER SUPPLY FOR A TATTOO MACHINE

(75) Inventors: Steve A. Copeland, Barrie (CA); Dean Byrnes, Kingston (CA); Ben Campbell, Kingston (CA)

(73) Assignee: Eikon Device Inc., Kingston, Ontario (CA)

( * ) Notice: Subject to any disclaimer, the term of this patent is extended or adjusted under 35 U.S.C. 154(b) by 160 days.

(21) Appl. No.: 11/939,118

(22) Filed: Nov. 13, 2007

(65) Prior Publication Data

US 2009/0125049 A1 May 14, 2009

(51) Int. Cl.
| | |
|---|---|
| *H05K 7/00* | (2006.01) |
| *H05K 5/00* | (2006.01) |
| *H02B 1/00* | (2006.01) |
| *H02B 1/26* | (2006.01) |
| *A61B 17/34* | (2006.01) |
| *B43K 5/00* | (2006.01) |

(52) U.S. Cl. .............. 361/679.01; 606/185; 606/186; 361/601; 361/622; 361/679.21; 81/9.22

(58) Field of Classification Search .............. 361/622, 361/601, 679.01, 679.21; 606/185–186; 81/9.22

See application file for complete search history.

(56) References Cited

U.S. PATENT DOCUMENTS

| | | | |
|---|---|---|---|
| 4,159,659 A | | 7/1979 | Nightingale |
| 4,705,038 A | * | 11/1987 | Sjostrom et al. .............. 606/180 |
| 4,903,696 A | * | 2/1990 | Stasz et al. ....................... 606/37 |
| 5,054,339 A | * | 10/1991 | Yacowitz ........................ 81/9.22 |
| 5,217,455 A | * | 6/1993 | Tan ..................................... 606/9 |
| 5,269,794 A | * | 12/1993 | Rexroth ......................... 606/180 |
| 5,290,273 A | | 3/1994 | Tan |
| 5,363,843 A | * | 11/1994 | Daneshvar .................... 128/897 |
| 5,383,874 A | * | 1/1995 | Jackson et al. .................... 606/1 |
| 5,401,242 A | * | 3/1995 | Yacowitz ......................... 604/48 |
| 5,540,683 A | * | 7/1996 | Ichikawa et al. ................. 606/40 |
| 5,551,319 A | * | 9/1996 | Spaulding et al. ............. 81/9.22 |
| 5,632,759 A | * | 5/1997 | Rexroth ......................... 606/180 |
| 5,662,644 A | * | 9/1997 | Swor ................................. 606/9 |
| 5,810,764 A | * | 9/1998 | Eggers et al. ................... 604/23 |
| 5,871,481 A | * | 2/1999 | Kannenberg et al. ........... 606/34 |
| 5,894,322 A | * | 4/1999 | Hamano et al. ................. 348/68 |
| 6,175,688 B1 | * | 1/2001 | Cassidy et al. ................ 392/470 |
| 6,231,569 B1 | * | 5/2001 | Bek et al. ......................... 606/34 |
| 6,235,020 B1 | | 5/2001 | Cheng et al. |
| 6,273,886 B1 | * | 8/2001 | Edwards et al. ................. 606/34 |
| 6,282,987 B1 | * | 9/2001 | Moniz ............................ 81/9.22 |
| 6,334,068 B1 | * | 12/2001 | Hacker ......................... 600/545 |

(Continued)

OTHER PUBLICATIONS

Canada Communicable Disease Report "Infection Prevention and Control Practices for Personal Services: Tattooing, Ear/Body Piercing and Electrolysis", vol. 25S3 (ISSN 1188-4169) published Jul. 1999.*

*Primary Examiner* — Jayprakash N Gandhi
*Assistant Examiner* — Bradley H Thomas
(74) *Attorney, Agent, or Firm* — Sand & Sebolt

(57) ABSTRACT

A power supply that includes a housing for retaining the electronic components needed to operate a tattoo machine. The housing includes a first region in which the tattooing controls are located and a second region that includes a display screen. The first and second regions are separated from each so that a plastic covering can be drawn over only the first region to protect the tattooing controls while leaving the display screen unobscured.

28 Claims, 11 Drawing Sheets

U.S. PATENT DOCUMENTS

| | | | |
|---|---|---|---|
| 6,494,880 B1 * | 12/2002 | Swanson et al. | 606/40 |
| 6,530,919 B1 * | 3/2003 | Chodorow et al. | 606/13 |
| 6,550,356 B1 | 4/2003 | Underwood | |
| 6,596,007 B2 * | 7/2003 | Evans | 606/186 |
| 6,720,776 B2 * | 4/2004 | Anderson et al. | 324/555 |
| 6,772,656 B2 | 8/2004 | Godoy et al. | |
| 6,950,004 B2 * | 9/2005 | Godoy et al. | 336/160 |
| 7,025,774 B2 * | 4/2006 | Freeman et al. | 606/181 |
| 7,207,242 B1 * | 4/2007 | Daigle | 81/9.22 |
| 7,340,980 B2 * | 3/2008 | Conti Vecchi | 81/9.22 |
| 7,442,042 B1 | 10/2008 | Lewis | |
| 7,572,251 B1 * | 8/2009 | Davison et al. | 604/500 |
| 7,748,294 B2 * | 7/2010 | Jarboe et al. | 81/9.22 |
| 2001/0001314 A1 * | 5/2001 | Davison et al. | 606/41 |
| 2002/0000231 A1 * | 1/2002 | McNeirney et al. | 128/849 |
| 2002/0087179 A1 * | 7/2002 | Culp et al. | 606/167 |
| 2002/0111713 A1 * | 8/2002 | Wang et al. | 700/245 |
| 2003/0032951 A1 * | 2/2003 | Rittman et al. | 606/34 |
| 2003/0199863 A1 * | 10/2003 | Swanson et al. | 606/40 |
| 2004/0097117 A1 * | 5/2004 | Gonnering | 439/218 |
| 2004/0116922 A1 * | 6/2004 | Hovda et al. | 606/41 |
| 2004/0179332 A1 * | 9/2004 | Smith et al. | 361/681 |
| 2005/0051416 A1 * | 3/2005 | Mahoney et al. | 200/512 |
| 2005/0080407 A1 * | 4/2005 | Ehr et al. | 606/32 |
| 2005/0203496 A1 * | 9/2005 | Ritchie et al. | 606/15 |
| 2006/0064080 A1 * | 3/2006 | Cao | 606/10 |
| 2006/0189468 A1 * | 8/2006 | DeMatteis et al. | 493/276 |
| 2006/0217700 A1 * | 9/2006 | Garito et al. | 606/34 |
| 2007/0250098 A1 * | 10/2007 | Malackowski et al. | 606/170 |
| 2008/0078271 A1 * | 4/2008 | Atkinson | 81/9.22 |
| 2008/0245546 A1 * | 10/2008 | Sutter | 174/66 |

* cited by examiner

POWER SUPPLY FOR A TATTOO MACHINE

CROSS-REFERENCE TO RELATED APPLICATIONS

This application is being filed concurrently with a U.S. Design patent application entitled POWER SUPPLY FOR A TATTOO MACHINE, the disclosure of which is incorporated herein by reference.

BACKGROUND OF THE INVENTION

1. Technical Field

This invention generally relates to power supplies. More particularly, the invention relates to a power supply for a tattoo machine. Specifically, the invention relates to a power supply in which the controls for tattooing are at one end of the device and the display screen is at the opposite end thereof, so as to permit selective sanitary covering of only the tattooing controls end of the supply during use, thereby leaving the display screen clearly visible.

2. Background Information

The trend for applying tattoos to the skin has been rapidly increasing over the last several years. The tattoos are applied by a tattoo artist who utilizes a powered needle to deliver colored ink in a pattern to an area just below the surface of the skin. Some of these powered needles form part of hand-held pen-like devices which reciprocate the needle and thereby make multiple punctures in the skin. Some of these pen-like devices may be connected to a power supply which is adjustable to allow the artist to regulate the intensity of the motion of the needle. The artist can adjust the power supply to regulate the frequency of the needle's reciprocation and the depth to which the needle will penetrate the client's skin. For example, the power supply will be set to provide a high current in order to plunge the needle deep into the skin for creating the image outlines, then adjusted to a lower current for plunging the needle to a shallower depth to shade between the lines.

The tattoo business is risky in nature because of the utilization of needles in puncturing of the client's skin during intradermal application of ink. The potential for disease transmission is of concern and consequently health departments tend to crack down on tattoo parlors by passing new health regulations and conducting spot inspections in order to safeguard both employees and clients. These regulations typically require that the tattoo artist utilize single use gloves, needles, plastic covers for power supplies, plastic sleeves for power cords and covers for the hand-held portion of the tattoo machine. All of these single use articles have to be disposed of after servicing each client and the entire area, including the power supply, must be cleansed with an approved disinfectant. New protective materials must then be applied to all of the equipment.

The global tattoo business is a relatively small market and as tattoo power supplies can last a decade or more, the vast majority of manufacturers utilize jobber boxes or enclosures as the housing for a tattoo machine power supply. Jobber boxes are basically rectangular metal boxes that are available in a variety of colors and sizes. The manufacturer drills the necessary holes in the jobber box so that knobs, controls and any other components can be mounted thereon. Jobber boxes, however, have many shortcomings in regards to executing sanitation regulations. For instance, all jobber boxes that are used as power supply housings include at least one large rotary knob that protrudes outwardly away from the box. This knob and any other controls may be manipulated several times by the artist during a single session. The area around the controls is typically not sealed against liquid penetration caused by having to spray disinfectant on the supply and this puts the wiring and other components housed within the box at risk during sanitization procedures. Furthermore, because of the sanitary regulations the controls must be covered during use. Most of the time, an artist will place a small plastic bag over the knobs and other controls to protect the same. This aids in preventing the controls from becoming contaminated as the artist moves back and forth between handling the client's skin and touching the controls. The power supplies also typically include a digital display or analogue gauges so that the artist can track how much he is adjusting the device. The plastic bags that are slid onto the power supply to cover the knobs and controls frequently tend to obscure the display screens and have to be moved so that the artist can see the display more clearly. This tends to uncover the knobs which have to be protected, leaving them open to contamination. It is therefore frequently necessary to physically remove the knobs from the power supply in order to sanitize them properly.

In addition to these shortcomings, the tattoo machine with its power supply is typically owned by the artist who will often travel and work in different tattoo parlors. Consequently, the tattoo machine and power supply will often be moved from one tattoo parlor to another. While the power supplies are typically fairly small, being approximately 8" wide and around 4 inches high, they are generally quite heavy and a little difficult to maneuver. Furthermore, jobber boxes are all rectangles and the knobs and displays are mounted externally and protrude outwardly away from the exterior wall of the box. The power supply is also usually placed on a desk height counter or a small shelf just under the counter to keep the display and control knobs accessible to the artist. The artist's head and eyes will typically be higher than the counter top or shelf so front mounted display screens are not optimum for viewing ease. Also, when the jobber box is placed on a shelf just under a counter, top mounted knobs prove to be difficult to access and adjust. The protruding knobs also cause additional problems in that they are prone to be impacted as the jobber box is moved from one location to another. One of the most common failures of these jobber box type power supplies is the tendency for knobs and controls to be broken off or damaged as the power supply is moved from one location to another.

There is therefore a need in the art for an improved tattoo machine power supply that addresses the shortcomings of the prior art devices.

SUMMARY OF THE INVENTION

The device of the present invention comprises a power supply that includes a housing for retaining the electronic components needed to operate a tattoo machine. The housing includes a first region in which the controls are located and a second region that includes a display screen. The first and second regions are separated from each so that a plastic covering can be drawn over only the first region to protect the controls while leaving the display screen unobscured. The first region slopes upwardly from the front wall of the housing to the rear wall thereof so that the controls are easily seen and ergonomically operable. The second region extends above the first region to protect the controls from possible impact. A portion of the second region slopes rearwardly from the front wall toward the rear wall and at an angle of about thirty degrees to vertical. The sloped portion of this second region includes the display screen. The angle on this sloped portion enables the display screen to be easily seen during use of the tattoo machine.

BRIEF DESCRIPTION OF THE DRAWINGS

The preferred embodiments of the invention, illustrative of the best mode in which applicant has contemplated applying the principles, are set forth in the following description and are shown in the drawings and are particularly and distinctly pointed out and set forth in the appended claims.

DETAILED DESCRIPTION OF THE INVENTION

Figure 7:
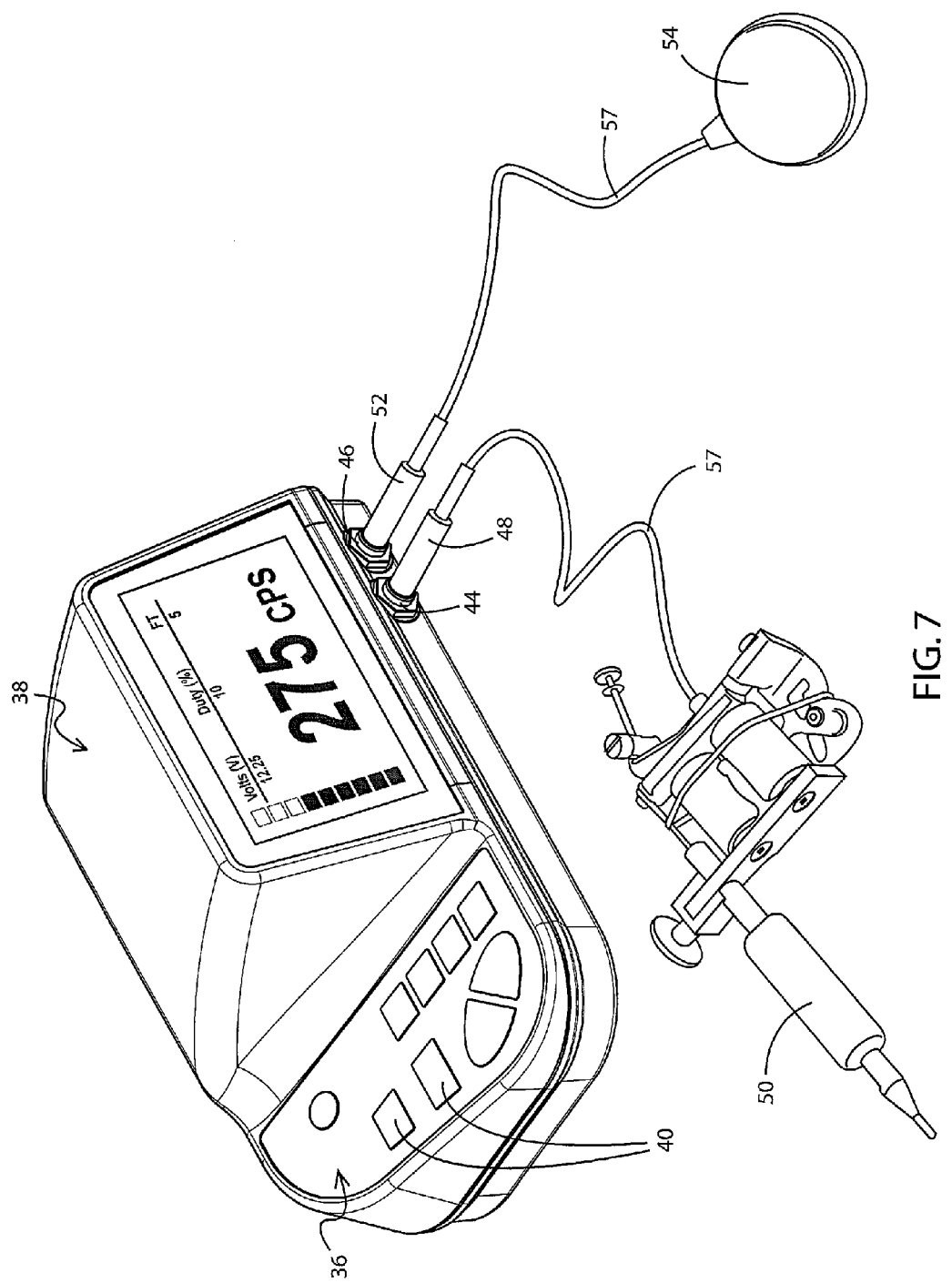
FIG. 7 is a perspective view of the power supply connected to a tattoo machine and a foot operated speed controller.
Figure 8:
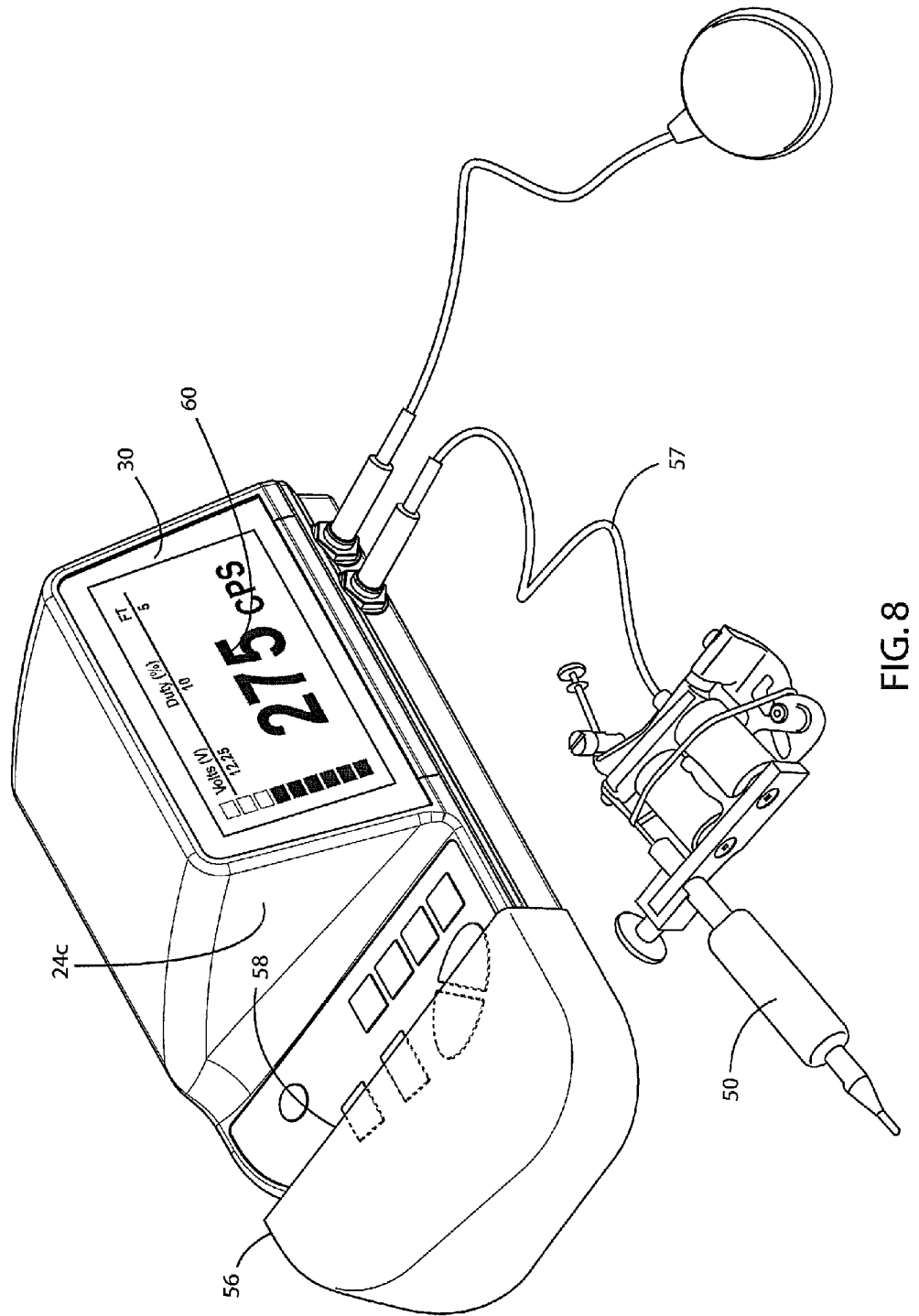
FIG. 8 is a perspective view of the power supply with a protective covering shown partially drawn over the tattooing controls.

Referring to FIGS. 1-9, there is shown a power supply in accordance with the present invention and generally indicated at 10. Power supply 10 comprises a housing 12 having an exterior wall 12a that defines an interior cavity (not shown). The interior cavity houses a plurality of electrical components (not shown) for driving a hand-held tattoo machine 50 (FIG. 7).

Exterior wall 12a includes a bottom wall 14, a front wall 16, a rear wall 18, side walls 20, 22 and a top wall 24. Top wall 24 is shaped and includes a first section 24a, a second section 24b and an intermediate section 24c. Front wall 16 extends from side wall 20 to side wall 22. Front wall 16 includes a first area 16a adjacent side wall 20 and a second area 16b adjacent side wall 22. First area 16a extends upwardly from bottom wall 14 to first section 24a of top wall 24 and terminates in a first front edge 26. First front edge 26 is spaced a distance D1 away from bottom wall 14. Second area 16b extends upwardly from bottom wall 14 to second section 24b of top wall 24 and terminates in a second front edge 28. Second front edge 28 is spaced a distance D2 away from bottom wall 14 and, as shown in FIG. 1, D2 is greater than D1.

Figure 2:
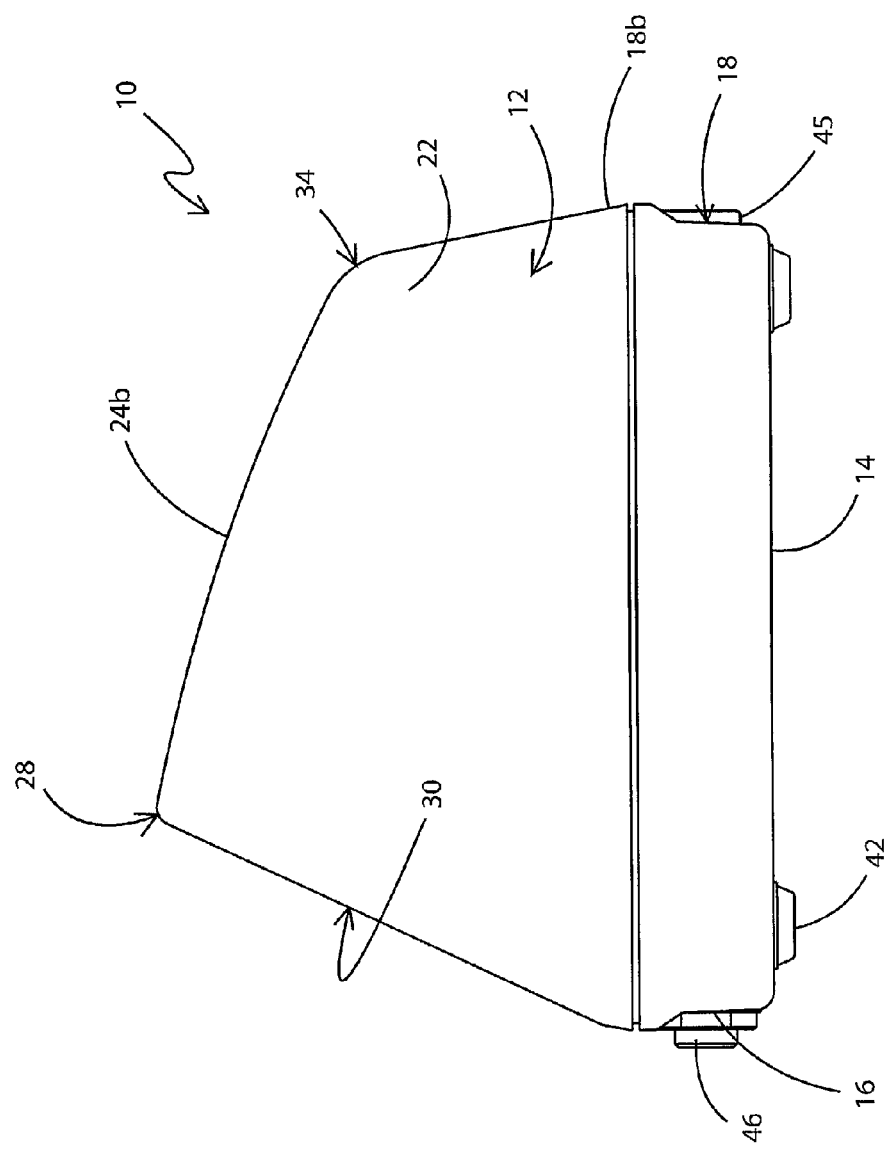
FIG. 2 is a first side view of the power supply of FIG. 1.

In accordance with a specific feature of the present invention, second area 16b extends vertically upwardly from bottom wall 14 until substantially level with first front edge 26. Second area 16b then slopes rearwardly at an angle of between twenty degrees and forty degrees from vertical toward back wall 18 (FIG. 2). The angle of display screen 30 preferably is thirty degrees from vertical. This sloped portion of second area 16b includes a display screen 30. Display screen 30 is rearwardly inclined to make it easier for the artist to see information displayed thereon while he or she is working. FIG. 2 also shows that second front edge 28 is spaced intermediate front and back walls 16, 18.

Figure 3:
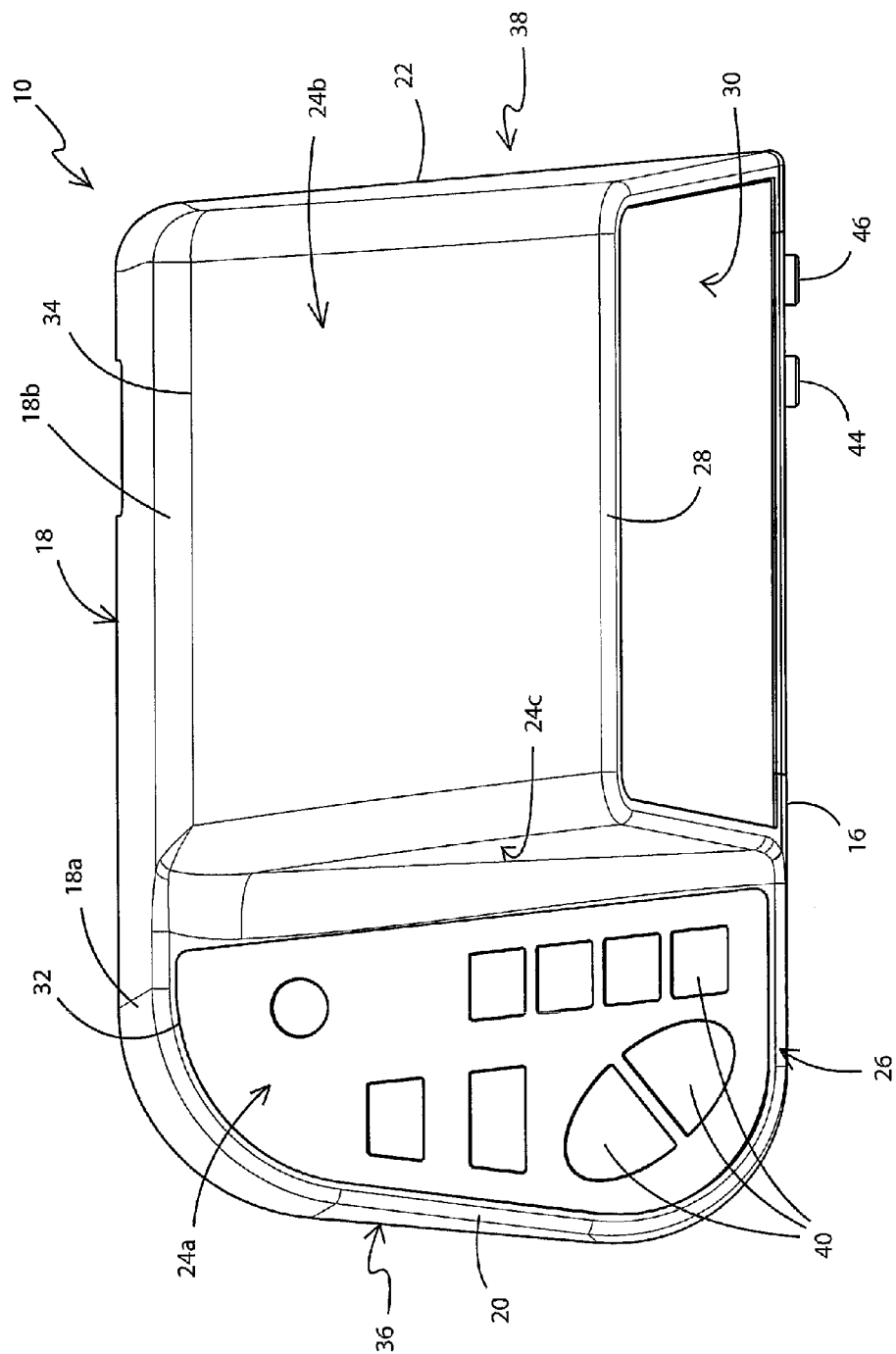
FIG. 3 is a top view of the power supply of FIG. 1.
Figure 4:
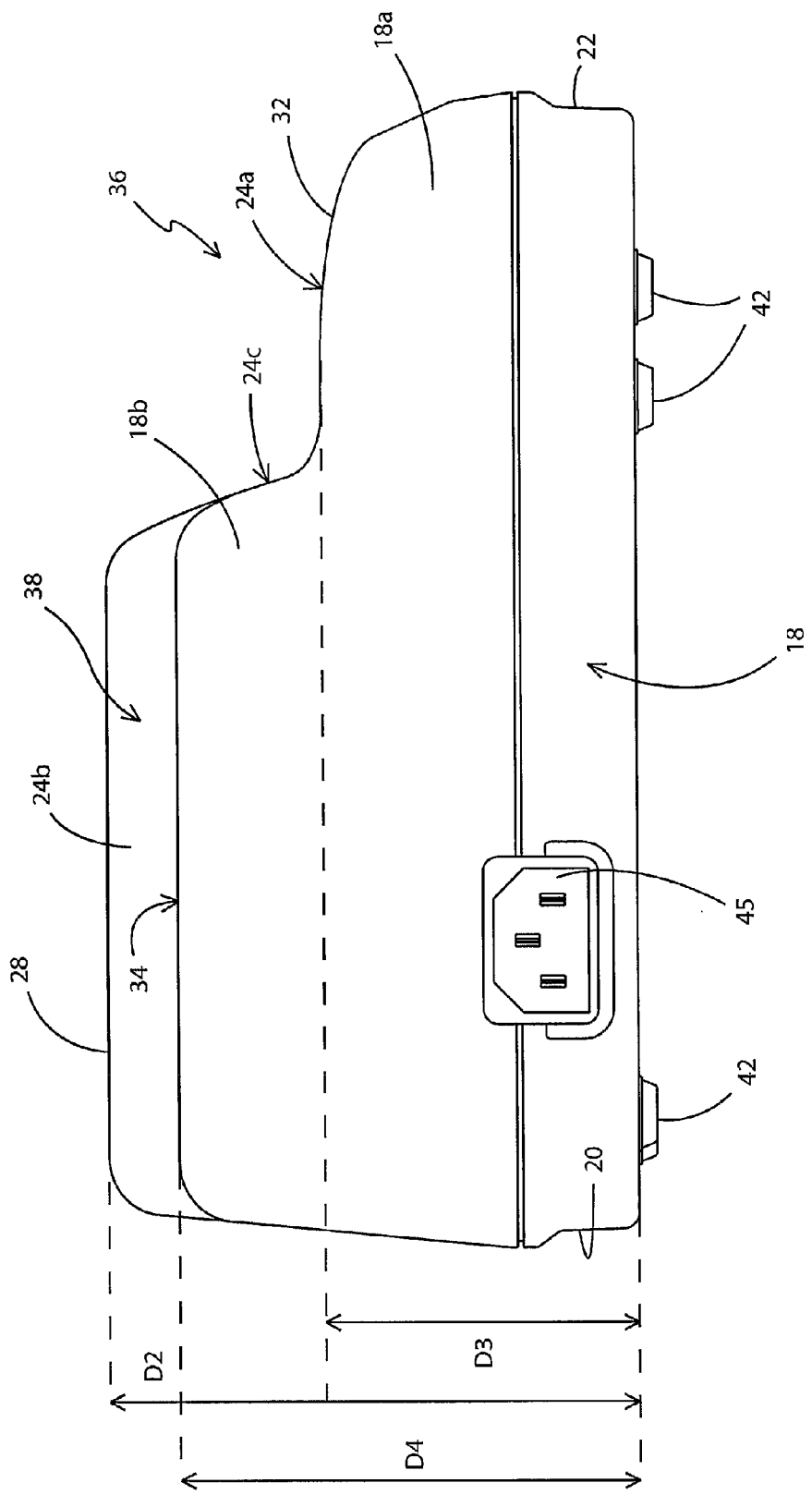
FIG. 4 is a rear elevational view of the power supply of FIG. 1.
Figure 5:
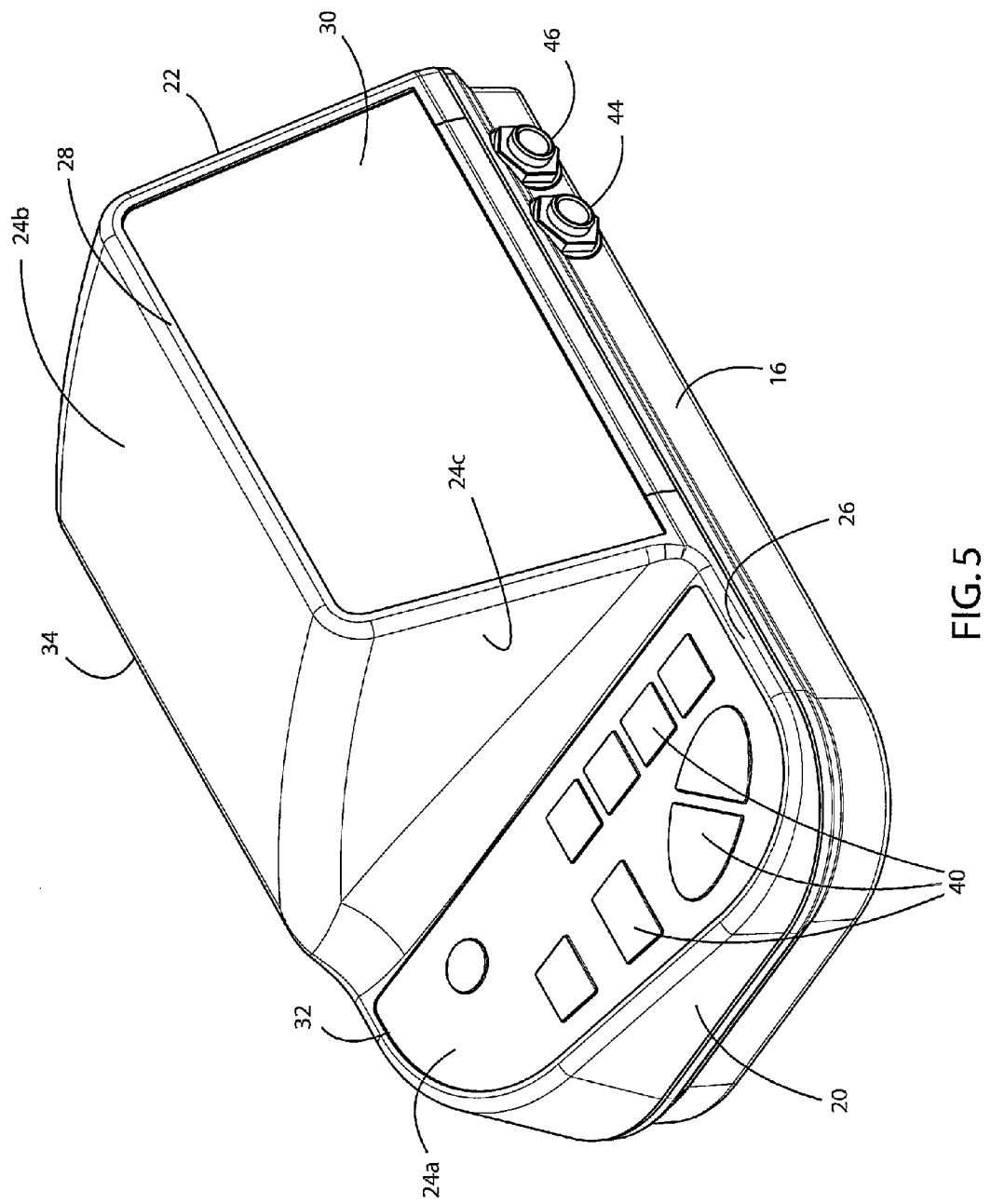
FIG. 5 is a perspective view of the power supply of FIG. 1.
Figure 6:
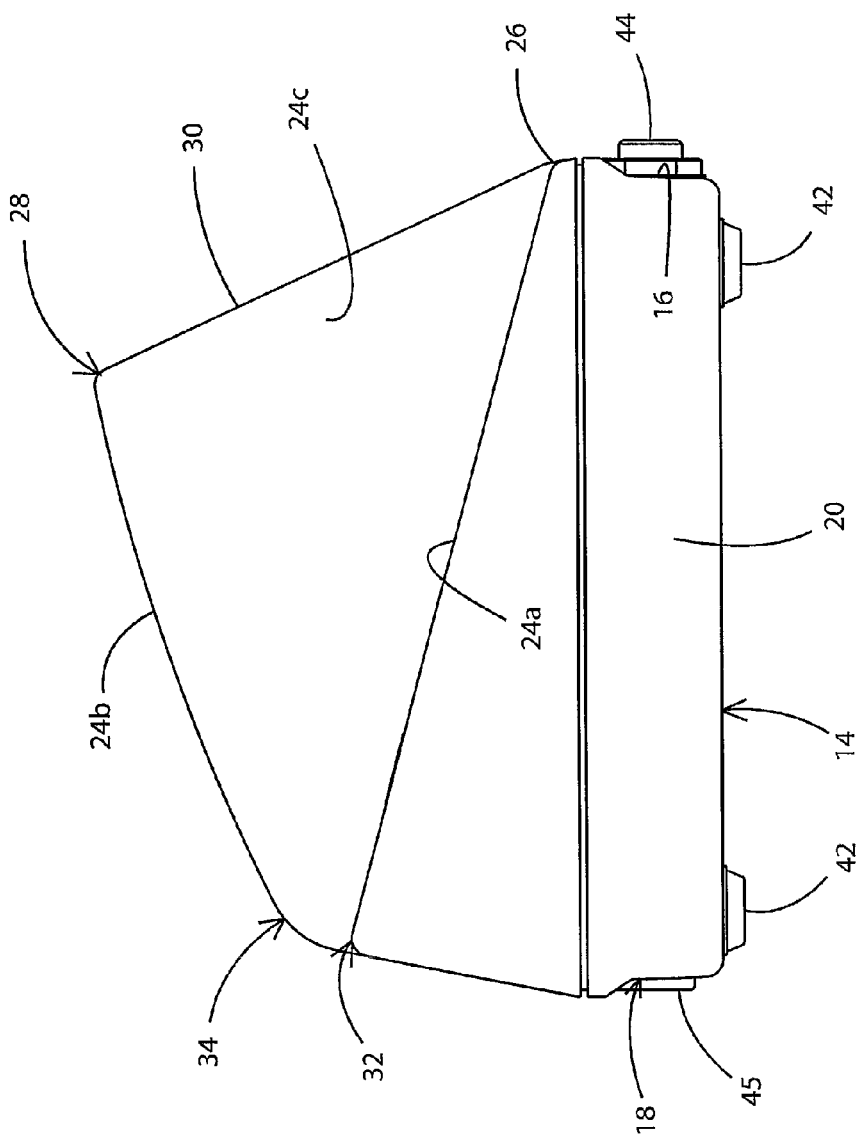
FIG. 6 is a second side view of the power supply of FIG. 1.

Referring to FIGS. 2-4, rear wall 18 extends from side wall 20 to side wall 22 and includes a first area 18a proximate side wall 20 and a second area 18b proximate side wall 22. In the first area 18a, rear wall 18 extends from bottom wall 14 to first section 24a of top wall 24 and terminates in a first rear edge 32. First rear edge 32 is spaced a distance D3 away from bottom wall 14. In the second area 18b, rear wall 18 extends from bottom wall 14 to second section 24b of top wall 24 and terminates in a second rear edge 34. Second rear edge 34 is spaced a distance D4 away from bottom wall 14. As shown in FIG. 4, distance D4 is greater than distance D3.

Figure 1:
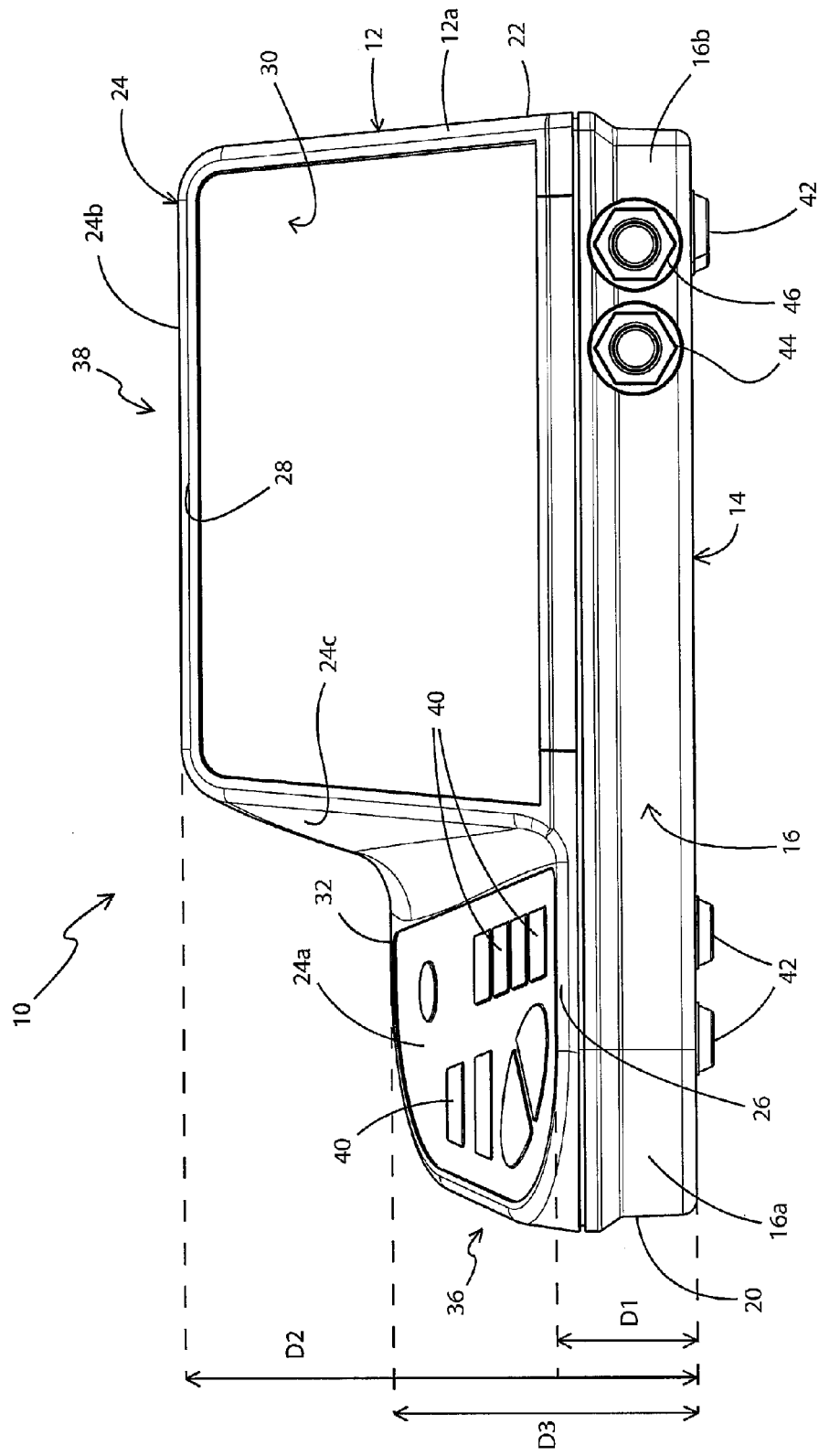
FIG. 1 is a front elevational view of a tattoo machine power supply in accordance with the present invention.

In accordance with a specific feature of the present invention and referring to FIGS. 1 and 4, it may be seen that D3 is greater than D1. Consequently, first section 24a of top wall 24 slopes upwardly from first front edge 26 toward first rear edge 32. The portion of the housing extending between first area 16a and second area 18a and including first section 24a of top wall 24 comprises a first region 36 of power supply 10.

In accordance with another specific feature of the present invention and referring to FIGS. 2-4, the portion of the housing that extends between second area 16b and second area 18b and includes display screen 30 and second section 24b of top wall 24, comprises a second region 38 of power supply 10. First and second regions 36, 38 of power supply 10 are disposed laterally adjacent each other and the division point between the two regions is essentially the intermediate section 24c of top wall 24. As shown in FIG. 1 intermediate section 24c is substantially vertical and separates the lower first region 36 from the higher second region 38. First region 36 is therefore effectively recessed relative to second region 38.

In accordance with yet another specific feature of the present invention, first region 36 includes one or more control members 40. Each of these control members 40 is operationally linked to an electronic component housed within the interior cavity of power supply 10 and is provided to be used during tattooing of the client. Each of the control members 40 is preferably substantially flush with first section 24a of top wall (FIG. 6) and essentially no portions of said control members 40 project outwardly beyond first section 24a, thereby reducing the possibility of control members 40 being damaged by objects impacting the same. Control members 40 shown in FIGS. 1-9 preferably are of a membrane type that is sealed against liquid penetration. All of the tattooing control members 40 are located in first region 36. The slope on first section 24a of top wall 24 provides ease of both access and sight for the artist. Furthermore, because first region 36 is substantially recessed relative to second region 38, control members 40 are protected against impact and potential damage.

In accordance with another feature of the present invention, display screen 30 is located entirely within second region 38 of power supply 10. As such, display screen 30 is spaced a distance away from the tattooing control members 40, Consequently, the tattooing control members 40 are located in a discrete first region 36 of power supply 10 and the display screen 30 is located in a second discrete region 38 of power supply 10. Any other controls (not shown) which are not used during tattooing and will therefore not become contaminated with bodily fluids, may be provided in the second region 38. Examples of such controls could be an on-off switch for the power supply 10 or an on-off switch or brightness controller for the screen itself. These non-tattooing controls will be activated before the tattooing procedure is begun and may either be deactivated after the tattooing procedure is completed or can be left in a preset position even when power supply 10 is not in use. The separation of the tattooing control members 40 from display screen 30 is important in that it allows the tattooing control members 40 to be separately covered to prevent contamination during use but, at the same time, allows the artist to clearly see display screen 30 while he works.

Power supply 10 further includes a plurality of legs 42 that extend downwardly from bottom wall 14 to engage a planar surface and thereby keep bottom wall 14 spaced a distance away therefrom. This allows heat to escape from power supply 10. Power supply 10 further includes a first and a second jack 44, 46, which are both disposed on front wall 16 beneath display screen 30. One of first and second jacks 44, 46 is designed to receive a first power connector 48 of a cable that operationally links power supply 10 to the hand-held tattoo machine 50. The other of first and second jacks 44, 46 is designed to receive a second connector 52 of a cable that operationally links power supply 10 to a foot-operated speed controller 54. Power supply 10 also includes an electrical socket 45 in rear wall 18 to receive an electrical cord (not shown) so that power supply 10 can be connected to an AC source.

Figure 9:
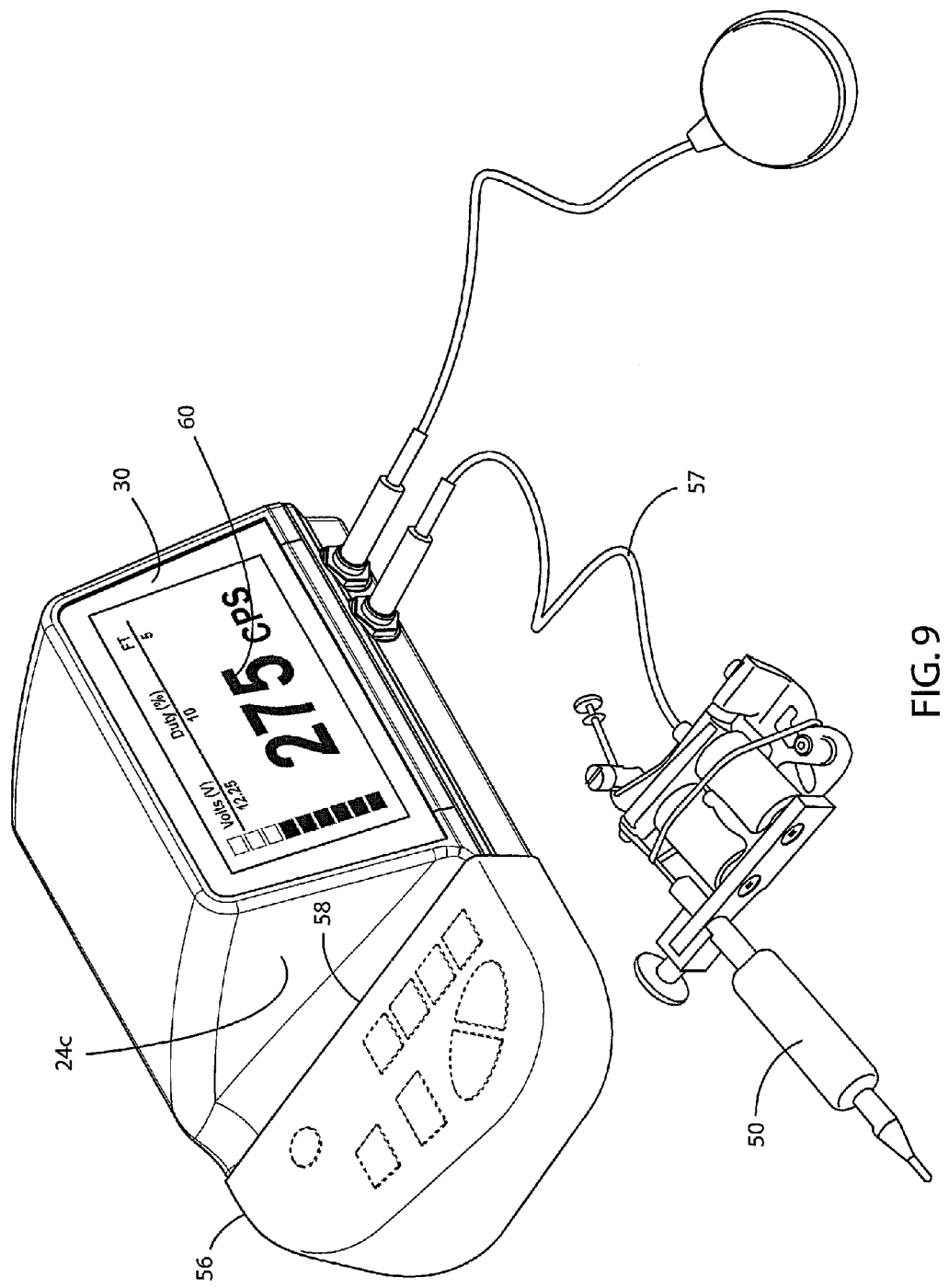
FIG. 9 is a perspective view of the power supply showing the protective cover pulled fully over the tattooing controls which are thereby protected against contamination.

In operation, power supply 10 is connected to tattoo machine 50 and to foot operated speed controller 54. Before the artist begins his/her work on the client, they must cover the tattooing control members 40 with a protective covering, such as a small plastic bag 56. In order to do this, the end of power supply 10 that houses control members 40 is lifted slightly off the planar surface upon which the device rests. Plastic bag 56 is opened and is slipped over the first region 36 of power supply 10 so that a first side of bag 56 is adjacent top wall 24a and a second side of bag 56 is adjacent bottom wall 14 and free ends of some of legs 42. Bag 56 is moved inwardly until the edge 58 of bag 56 engages intermediate section 24c of top wall 24. Intermediate section 24c substantially prevents bag 56 from being drawn any further across power supply 10. FIG. 9 shows that all of the tattooing control members 40 that are housed in first region 36, are completely covered by bag 56. The entire display screen 30, however, is free of any protective covering and may therefore be easily seen by the artist. Furthermore, bag 56 does not contact jacks 44, 46 and therefore does not interfere with the cables 57 that extend between jacks 44, 46 and tattoo machine 50 and speed controller 54. The cables 57 also do not interfere with the bag 56 and therefore do not prevent the bag 56 from being completely pulled over control members 40.

Once bag 56 is in position and is covering first region 36, the artist places power supply 10 on an appropriate planar surface. That planar surface may be either at counter top height or on a shelf, as the inclined display screen 30 allows the artist to easily view the same. When the artist is ready to work, he engages the appropriate tattooing control members 40 by pushing down on bag 56 to set the initial output, such as the voltage, current etc., from power supply 10. If a non-tattooing control, such as an on-off switch, is located on second region 38 instead of first region 36, that non-tattooing control does not need to be covered as it will not be touched at all during the tattooing procedure. Such a control will be engaged prior to the artist beginning his work and will not be touched until after the tattoo is completed, the bag 56 is removed and it is time to decontaminate power supply 10.

When the artist is ready to tattoo his client, he uses a foot to engage speed controller 54 to activate the electronic components within power supply 10 and thereby provide power to the handheld tattoo machine 50. Display screen 30 shows information 60 thereon to indicate to the artist the levels that the various control members 40 are set at. When the artist wishes to adjust any one of the electrical outputs from power supply 10, such as the current in order to adjust the action of the needle(s) in tattoo machine 50, he engages the appropriate one of the control members 40 through bag 56, checks the information 60 displayed on display screen 30 and continues his work. In a single session, the artist will likely need to adjust the settings on power supply 10 via the tattooing control members 40 and check the display screen 30 several times. When the tattoo on the client is completed, the power supply 10 is deactivated. If the on-off switch is part of the control members 40, then power supply 10 is deactivated by engaging the appropriate control member 40 through bag 56. If the on-off switch is not part of control members 40 and is located on second region 38, then this switch will not be touched until bag 56 is slid off from first region 36 of power supply 10 and is disposed of in accordance with the appropriate health regulations. After bag 56 is removed and the artist has decontaminated his hands, the switch will be engaged to shut off the power supply. The entire housing of power supply 10 will then be cleaned with an appropriate disinfectant.

In accordance with another specific feature of the present invention, the housing of power supply 10 preferably is injection molded from a suitable plastic material. This reduces the weight of power supply 10, making it easier for the artist to take the supply from one location to another. Furthermore, the plastic is water repellant and is easily cleaned and disinfected to comply with health regulations.

Figure 10:
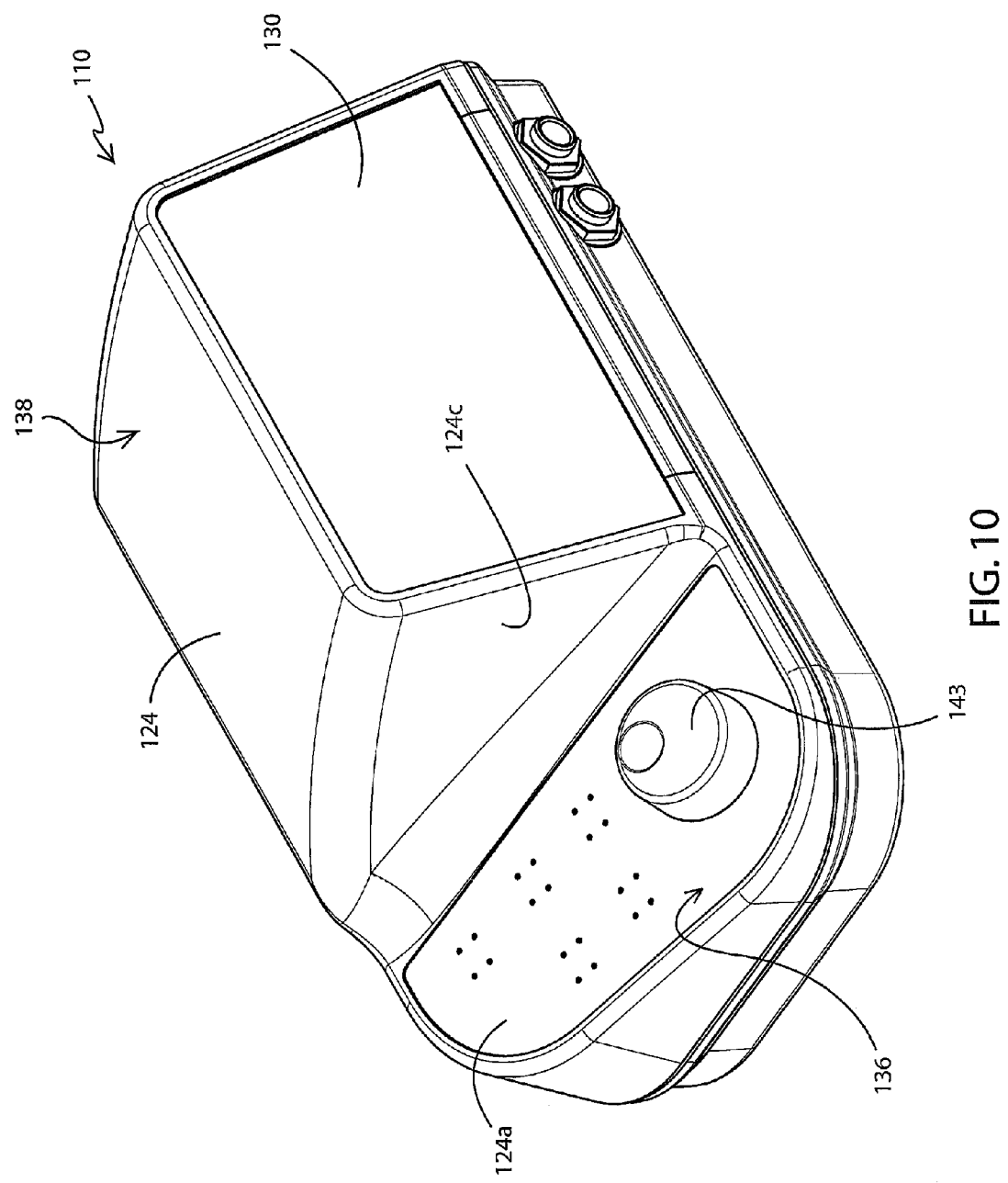
FIG. 10 is a perspective view of a second embodiment of a tattoo machine power supply in accordance with the present invention showing an alternative type of tattooing control.

A second embodiment of a power supply is shown in FIG. 10 and is generally referenced at 110. Power supply 110 is substantially identical to power supply 10, with the exception that the control members may be touch type or push button controls and/or at least one rotary knob 143. Knob 143 preferably has a fairly wide operating range, being rotatable through around five turns or 1800 degrees. As with the previous power supply 10, power supply 110 has the control members 140 all located in a first region 136 that is separate and discrete from a second region 138 that includes a display screen 130. Rotary knob 143 extends outwardly away from top wall 124 of power supply 110, but its positioning adjacent intermediate section 124c of top wall 124, affords knob 143 protection from impact as supply 110 is moved between locations. Additionally, because of the slope on first section 124a of top wall 124, knob 143 is relatively easily accessed no matter where power supply 110 is set up. A protective bag may be drawn over the first region 136 to cover control members 140 during use of power supply 110. Power supply 110 is used in substantially the same manner as power supply 10.

Figure 11:
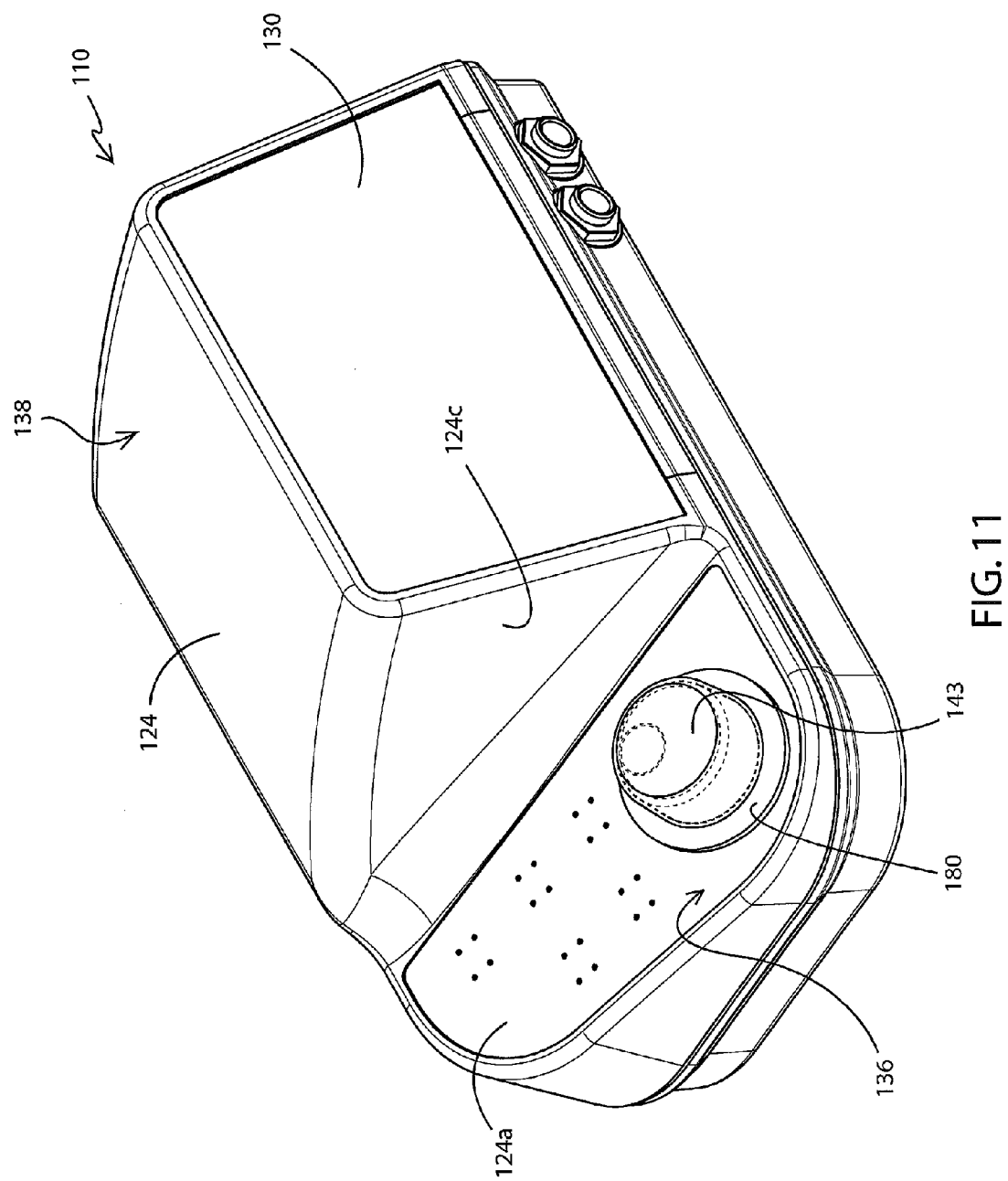
FIG. 11 is a perspective view of the power supply of FIG. 10 shown with a blister shield shown covering the tattooing control to protect the same from contamination during the tattooing procedure.

FIG. 11 shows one or more of the tattooing control members, such as knob 143, being covered in an alternate manner by positioning a custom-made complementary sized and shaped blister shield 180 over the same. Blister shield 180 may be configured to cover just one of the components, rotary knob 143, for example, or may extend across the entire first region 136 covering some or all of the tattooing control members. Blister shield 180 is manufactured from any suitable material that permits the artist to engage and thereby adjust the tattooing control members 140 during the tattooing procedure.

The power supply of the present invention addresses some of the issues and problems found in prior art devices. For example, the slope of first section 24a of top wall 24 provides good visibility for the artist to see and utilize the tattooing control members 40 provided thereon. The slope also gives the artist good ergonomic access to those control members 40. Similarly, the inclined display screen 30 also gives the artist good visibility for viewing information 60 displayed thereon. The fact that the device is arranged so that tattooing control members 40 may be covered independent of display screen 30, aids the artist in monitoring the outputs from power supply 10 while being able to easily adjust the controls without contaminating control members 40. The materials used in the manufacture of the housing also aids in improving the ease of disinfecting the supply after each use and in reducing the overall weight of the supply. The arrangement of the various components, especially having the control members 40 positioned in such a manner that they are recessed relative to second region 38, also aids in protecting control members 40 from impact during transport.

It will be understood that external shape of the power supply housing may be varied without departing from the spirit of the present invention. However, the housing of any other shaped power supply must be configured so that the control members are separated from the display screen and are easily covered independently of the display screen.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention are an example and the invention is not limited to the exact details shown or described.

The invention claimed is:

1. A power supply for a tattoo machine comprising:
a housing;
electronic components disposed within said housing;
one or more tattoo machine control members for manipulation by a user to permit operational adjustment of said tattoo machine; and
at least one external connection for connecting said power supply to said tattoo machine,
wherein said housing has a front wall and comprises:
a display region having opposed front and rear walls and first and second opposed side walls, wherein said display region front wall comprises a first portion of the front wall of the housing; a display screen and said display region front wall being free of all tattoo machine control members, and
a control region having a front wall comprising a second portion of the front wall of the housing, said control region comprising a tongue-like projection which extends laterally and longitudinally from proximate the front wall of the display region to proximate the rear wall of the display region, said one or more tattoo machine control members being disposed in said control region and said control region being free of all external connections, and wherein said control region is configured to receive a flexible removable protective cover thereon to substantially fully cover said control region and said one or more tattoo machine control members while permitting operation of said tattoo machine control members and not obstructing said display screen or the at least one external connection in the display region.

2. The power supply of claim 1 wherein the one or more tattoo machine control members are located on an upper surface of the control region.

3. The power supply of claim 1 wherein the one or more tattoo machine control members comprise one of a membrane type control and a push button type control.

4. The power supply of claim 1 wherein the one or more tattoo machine control members are flush with the upper surface of said control region.

5. The power supply of claim 1 wherein the one or more tattoo machine control members comprises at least one rotary knob extending upwardly from said upper surface of said control region.

6. The power supply of claim 1 wherein the at least one external connection is located on said front wall of said display region.

7. The power supply of claim 1 wherein an upper surface of said control region is substantially horizontal when the power supply is horizontally disposed.

8. The power supply of claim 1 wherein an upper surface of said control region is inclined at an angle and slopes upwardly from a front wall of said control region to a rear wall of said control region.

9. The power supply of claim 1 wherein said front wall of said display region is inclined at an angle.

10. The power supply of claim 9 wherein the angle is between twenty and forty degrees relative to vertical.

11. The electronic control unit of claim 1, wherein said control region is configured to be encased by said flexible removable protective cover.

12. The electronic control unit of claim 1, wherein said at least one external connection comprises a connection to the hand-held device.

13. In combination:
a power supply for a tattoo machine comprising:
a housing;
electronic components disposed within said housing;
one or more tattoo machine control members for manipulation by a user to permit operational adjustment of said tattoo machine;
at least one external connection for connecting said power supply to said tattoo machine,
wherein said housing has a front wall and comprises:
a display region having opposed front and rear walls and first and second opposed side walls, wherein said display region front wall comprises a first portion of the front wall of the housing; and a display screen, said display region front wall being free of all tattoo machine control members, and
a control region having a front wall comprising a second portion of the front wall of the housing, said control region comprising a tongue-like projection which extends laterally and longitudinally from proximate the front wall of the display region to proximate the rear wall of the display region, said one or more tattoo machine control members being disposed in said control region, and said control region being free of all external connections; and
a flexible removable protective cover which selectively is applied over the control region and the one or more tattoo machine control members thereon, said cover substantially fully covering said control region and said one or more tattoo machine control members while permitting operation of said tattoo machine control members and not obstructing said display screen nor any of the one or more external connections in the display region.

14. The power supply as defined in claim 1, wherein the housing further includes a rear wall opposed to the front wall, and wherein the rear wall of the display region comprises a first portion of the rear wall of the housing, and the control region has a rear wall that comprises a second portion of the rear wall of the housing, and wherein the tongue-like projection extends from proximate the front wall of the housing to proximate the rear wall of the housing.

15. The power supply as defined in claim 1, wherein the first and second portions of the front wall of the housing are aligned.

16. The power supply as defined in claim 1, wherein the first and second portions of the front wall of the housing are coplanar and substantially continuous with each other.

17. The power supply as defined in claim 1, wherein the display region is free of all tattoo machine control members.

18. The combination of claim 13, wherein said control region is configured to be encased by said flexible removable protective cover.

19. The combination of claim 18 wherein the removable protective cover is configured to conform to said control region of the power supply.

20. The combination of claim 18 wherein the removable protective cover comprises a blister shield or a plastic bag.

21. The combination of claim 18 further comprising:
    a second external connection on the display region; and
    a foot-operable speed controller engageable with the second external connector of the power supply.

22. The combination of claim 18, wherein said tongue-like projection of the electronic control unit extends laterally from proximate the front wall of the display region to proximate the rear wall of the display region.

23. The combination of claim 18 wherein said at least one external connection is located on one of said front wall, rear wall, first side wall or second side wall of said display region.

24. The combination of claim 18 wherein said display screen is disposed on a portion of said front wall of said display region.

25. The power supply as defined in claim 13, wherein the housing further includes a rear wall opposed to the front wall, and wherein the rear wall of the display region comprises a first portion of the rear wall of the housing, and the control region has a rear wall that comprises a second portion of the rear wall of the housing, and wherein the tongue-like projection extends from proximate the front wall of the housing to proximate the rear wall of the housing.

26. The power supply as defined in claim 18, wherein the first and second portions of the front wall of the housing are aligned.

27. The power supply as defined in claim 18, wherein the first and second portions of the front wall of the housing are coplanar and substantially continuous with each other.

28. The power supply as defined in claim 18, wherein the display region is free of all tattoo machine control members.

\* \* \* \* \*

UNITED STATES PATENT AND TRADEMARK OFFICE
CERTIFICATE OF CORRECTION

PATENT NO. : 7,969,715 B2
APPLICATION NO. : 11/939118
DATED : June 28, 2011
INVENTOR(S) : Copeland et al.

Page 1 of 2

It is certified that error appears in the above-identified patent and that said Letters Patent is hereby corrected as shown below:

Column 8, line 25 (Claim 11) "The electronic control unit" should be changed to
--The power supply--

Column 8, line 28 (Claim 12) Cancel the text beginning with "The electronic control" to and ending "hand-held device." in Column 8, line 30, and insert the following claim:

--12. The power supply of claim 1 wherein said at least one external connection is located on one of said front wall, rear wall, first side wall or second side wall of said display region.--

Column 8, line 31 (Claim 13) Cancel the text beginning with "In combination" to and ending "the display region." in Column 8, line 63, and insert the following claim:

--13. The power supply of claim 1 wherein said display screen is disposed on a portion of said front wall of said display region.--

Column 9, line 13 (Claim 18) Cancel the text beginning with "The combination of claim 13" to and ending "protective cover." in Column 9, line 15, and insert the following claim:

--18. In combination: a power supply for a tattoo machine comprising: a housing; electronic components disposed within said housing; one or more tattoo machine control members for manipulation by a user to permit operational adjustment of said tattoo machine; at least one external connection for connecting said power supply to said tattoo machine, wherein said housing has a front wall and comprises: a display region having opposed front and rear walls and first and second opposed side walls, wherein said display region front wall comprises a first portion of the front wall of the housing; and a display screen, said display region front wall being free of all tattoo machine control members, and a control region having a front wall comprising a second portion of the front wall of the housing, said control region comprising a tongue-like projection which extends laterally and longitudinally from proximate the front wall of the display region to proximate the rear wall of the display region, said one or more tattoo machine control members Signed and Sealed this
Tenth Day of July, 2012

David J. Kappos
*Director of the United States Patent and Trademark Office*

CERTIFICATE OF CORRECTION (continued)
U.S. Pat. No. 7,969,715 B2 being disposed in said control region, and said control region being free of all external connections; and a flexible removable protective cover which selectively is applied over the control region and the one or more tattoo machine control members thereon, said cover substantially fully covering said control region and said one or more tattoo machine control members while permitting operation of said tattoo machine control members and not obstructing said display screen nor any of the one or more external connections in the display region.--

Column 9, line 24 (Claim 21) "external connector" should be changed to --external connection--

Column 9, line 25 (Claim 22) Cancel Claim 22 beginning with ""The combination" and ending with "the display region." in Column 10, line 2, and insert the following claim:

--22. The combination of claim 18 wherein said control region is configured to be encased by said flexible removable protective cover.--

Column 10, line 9 (Claim 25) "as defined in claim 13" should be changed to --as defined in claim 18--